US012765570B2

(12) United States Patent
Ghassan Nuqul

(10) Patent No.: US 12,765,570 B2
(45) Date of Patent: Oct. 20, 2026

(54) BEVERAGE COMPOSITION CONTAINING EXTRACTS OF CAROB, ANISE, EUCALYPTUS AND/OR THYME

(71) Applicant: FINE HYGIENIC PAPER FZE, Dubai (AE)

(72) Inventor: Elia Ghassan Nuqul, Amman (JO)

(73) Assignee: Nuqul Brothers Company Limited, Amman (JO)

( * ) Notice: Subject to any disclaimer, the term of this patent is extended or adjusted under 35 U.S.C. 154(b) by 234 days.

(21) Appl. No.: 18/839,426

(22) PCT Filed: Feb. 17, 2022

(86) PCT No.: PCT/IB2022/051405
§ 371 (c)(1),
(2) Date: Aug. 17, 2024

(87) PCT Pub. No.: WO2023/156819
PCT Pub. Date: Aug. 24, 2023

(65) Prior Publication Data
US 2025/0194625 A1 Jun. 19, 2025

(51) Int. Cl.
*A23F 3/34* (2006.01)
*A61K 36/82* (2006.01)

(52) U.S. Cl.
CPC ................ *A23F 3/34* (2013.01); *A61K 36/82* (2013.01)

(58) Field of Classification Search
CPC .................................. A23F 3/34; A61K 36/82
See application file for complete search history.

(56) References Cited

U.S. PATENT DOCUMENTS 4,410,556 A * 10/1983 Lunder ..................... A23F 3/18 426/597
2006/0121158 A1* 6/2006 Ferruzzi .................... A23L 2/38 426/72

OTHER PUBLICATIONS

"Making tea with distilled water". Available online as of Sep. 2, 2010 from www.mypurewater.com. pp. 1-5. (Year: 2010).*
Ghassan Nuqul, E., PCT/IB2022/051405, International Search Report, Nov. 14, 2022, 3 pages.
Ghassan Nuqul, E., PCT/IB2022/051405, Written Opinion, Nov. 14, 2022, 4 pages.
Rtibi, K. et al., "*Certonia siliqua* L. (immature carob bean) inhibits intestinal glucose absorption, improves glucose tolerance and protects against alloxan-induced diabetes in rat", J. of the Science of Food and Agriculture, Oct. 2016, vol. 97, Issue 8, pp. 2664-2670 (Abstract).

(Continued)

*Primary Examiner* — Jenna A Watts
(74) *Attorney, Agent, or Firm* — Rahman LLC

(57) ABSTRACT

The invention relates to a nutritional supplement in form of a tea beverage which provides health and longevity benefits when consumed. The main composition of the invention includes carob, anise, eucalyptus and thyme. The composition may further include honey and micellized curcumin. The tea beverage may also contain other compositions such as green tea, manuka honey and similar natural herbs and ingredients with health benefits. The forms for this tea beverage composition include, without limitation, tea bags, loose-leaf tea (also sometimes referred to as loose or powdered tea), ready-to-drink beverages and tea in powder (or micronized powder) form.

20 Claims, 10 Drawing Sheets

| Ingredient | Amount per cup / daily intake |
|---|---|
| Anise* | Extract of 61.3 g raw material / 2 × |
| Thyme* | Extract of 9.2 g raw material / 2 × |
| Eucalyptus* | Extract of 6.1 g raw material / 2 × |
| Carob* | Extract of 12.3 g raw material / 2 × |
| Manuka honey* | 44.1 g / 2 × |
| Curcuminoids** | 33.8 mg curcumin, 1.3 mg demethoxycurcumin, 0.7 mg bis-demethoxycurcumin / 2 × |
| Vitamin D (cholecalciferol) | 6.0 mcg / 2 × |
| Vitamin B12 | 1.6 mcg / 2 × |
| Iodine | 27 mcg / 2 × |

* The ingredients (350 g of anise, 70 g of cut carob pots, 52.5 g of thyme, 35 g of eucalyptus, and 252 g of manuka honey) were added to 6.5 L of distilled water, boiled for 5 min, and brewed for 3 min. The infusion was filtered and cooled for 30 min. The tea was decanted into a cup (175 mL) and 10 drops of proprietary liquid curcumin formulation was added.
** Consisting of curcumin, demethoxycurcumin, and bis-demethoxycurcumin

(56) References Cited

OTHER PUBLICATIONS

Faried, M. et al., "Aqueous anise extract alleviated the pancreatic changes in streptozotocin-induced diabetic rat model via modulation of hyperglycemia, oxidative stress, apoptosis and autophagy: a biochemical, histological and immunohistochemical study", Folia morphologica, Poland, 2020, vol. 79, No. 3, pp. 489-502 (Abstract).

Gray A. et al., "Antihyperglycemic actions of *Eucalyptus globulus* (Eucalyptus) are associated with pancreatic and extra-pancreatic effects in mice", The Journal of Nutrition, Dec. 1998, vol. 128, No. 12, pp. 2319-2323 (Abstract).

Büyükbalci, A. et al., "Determination of in vitro antidiabetic effects, antioxidant activities and phenol contents of some herbal teas", Plant foods for human nutrition, Mar. 2008, vol. 63, No. 1, pp. 27-33 (Abstract).

Naksuriya, O. et al., "Curcumin nanoformulations: a review of pharmaceutical properties and preclinical studies and clinical data related to cancer treatment", Biomaterials, Mar. 2014, vol. 35, No. 10, pp. 3365-3383 (Abstract).

* cited by examiner

| Ingredient | Amount per cup / daily intake |
|---|---|
| Anise* | Extract of 61.3 g raw material / 2 × |
| Thyme* | Extract of 9.2 g raw material / 2 × |
| Eucalyptus* | Extract of 6.1 g raw material / 2 × |
| Carob* | Extract of 12.3 g raw material / 2 × |
| Manuka honey* | 44.1 g / 2 × |
| Curcuminoids** | 33.8 mg curcumin, 1.3 mg demethoxycurcumin, 0.7 mg bis-demethoxycurcumin / 2 × |
| Vitamin D (cholecalciferol) | 6.0 mcg / 2 × |
| Vitamin B12 | 1.6 mcg / 2 × |
| Iodine | 27 mcg / 2 × |

* The ingredients (350 g of anise, 70 g of cut carob pots, 52.5 g of thyme, 35 g of eucalyptus, and 252 g of manuka honey) were added to 6.5 L of distilled water, boiled for 5 min, and brewed for 3 min. The infusion was filtered and cooled for 30 min. The tea was decanted into a cup (175 mL) and 10 drops of proprietary liquid curcumin formulation was added.
** Consisting of curcumin, demethoxycurcumin, and bis-demethoxycurcumin

FIG 1

Table 1. Demographics of the study cohort.

| | Age | Employment | Education* | Smoker[x] | Physical activity | Per day (hours) | Frequency (per week) | Meals (per day) | Meals skipped | Snacks (per day) | Outside meals, fast food | Water intake (cups[‡]/day) |
|---|---|---|---|---|---|---|---|---|---|---|---|---|
| MEN | | | | | | | | | | | | |
| 1 | 40 | telecom engineer | 3 | Y - 2 | walking, swimming | 1-2 | 1-2 | 2 | breakfast | 1 | 1-3/mo | >5 |
| 2 | 27 | civil engineer | 4 | N - 0 | weightlifting, jogging | 1-2 | 4 | >3 | none | 2 | never | >5 |
| 3 | 27 | industrial technician | 1 | Y - 1 | horse riding | 2-3 | 1-2 | 3 | none | 1 | <1/mo | >5 |
| 4 | 30 | driver | 4 | N - 0 | none | 0 | 0 | 1 | breakfast, dinner | 2 | <1/mo | 3-5 |
| 5 | 29 | unemployed | 3 | Y - 1 | swimming | 1-2 | 2 | 2 | dinner | 1 | 1-3/mo | >5 |
| 6 | 33 | driver | 3 | Y - 1 | fitness exercises | 1-2 | 1-2 | 2 | lunch | 1 | 1-3/wk | >5 |
| 7 | 27 | engineer | 3 | N - 0 | weightlifting | 1-2 | 4 | >3 | none | 2 | 1-3/wk | >5 |
| 8 | 37 | did not disclose | 0 | N - 0 | none | 0 | 0 | 3 | none | 3 | 4-6/wk | >5 |
| 9 | 37 | administrative | 3 | Y - 3 | weightlifting | 1-2 | 3-4 | 2 | dinner | 2 | 1-3/mo | 3-5 |
| 10 | 41 | teacher | 3 | Y - 2 | none | 0 | 0 | 3 | none | 2 | 1-3/mo | >5 |
| 11 | 24 | unemployed | 3 | N - 0 | jogging | 1-2 | 1-2 | 2 | dinner | 2 | 1-3/wk | 3-5 |
| 12 | 43 | driver | 1 | Y - 1 | football | 1-2 | 1-2 | 3 | none | 2 | daily | 3-5 |
| 13 | 31 | unemployed | 2 | N - 0 | fitness exercises | <1 | 1-2 | 2 | breakfast, dinner | 2 | 1-3/wk | 3-5 |
| 14 | 41 | guard/ handyman | 1 | N - 0 | Swedish exercises | <1 | 3-4 | 2 | lunch | 3 | <1/mo | >5 |
| 15 | 39 | administrative | 1 | N - 0 | none | 0 | 0 | 2 | dinner | 1 | never | 1-3 |
| WOMEN | | | | | | | | | | | | |
| 1 | 42 | local NGO | 3 | N - 0 | none | 0 | 0 | 2 | dinner | 1 | 1-3/wk | >5 |
| 2 | 27 | dentist assistant | 3 | N - 0 | walking | <1 | 1-2/wk | 3 | none | 2 | <1/mo | 3-5 |
| 3 | 42 | unemployed | 2 | Y - 2 | aerobics/ machines | 1-2 | 3-4/wk | 2 | breakfast | 2 | <1/mo | >5 |
| 4 | 36 | logistics/ clearance | 3 | Y - 3 | none | 0 | 0 | 2 | breakfast | 2 | 1-3/wk | 3-5 |
| 5 | 33 | unemployed | 3 | N - 0 | none | 0 | 0 | 3 | none | 3 | 1-3/mo | 3-5 |
| 6 | 44 | secretary | 1 | N - 0 | walking | 1-2 | 3-4/wk | 3 | none | 1 | 1-3/mo | >5 |
| 7 | 30 | lab technician | 3 | N - 0 | none | 0 | 0 | 2 | dinner | 2 | 1-3/mo | 3-5 |
| 8 | 29 | unemployed | 4 | N - 0 | aerobics | 1-2 | 4/wk | 3 | none | 2 | 1-3/mo | 1-3 |
| 9 | 33 | mechanical technician | 3 | N - 0 | none | 0 | 0 | 2 | dinner | 1 | 1-3/mo | 3-5 |
| 10 | 39 | unemployed | 3 | N - 0 | cardio/machines | <1 | 3-4/wk | 3 | none | 2 | <1/mo | >5 |
| 11 | 57 | unemployed | 4 | Y - 1 | machines | 1-2 | 3-4/wk | >3 | none | 3 | 1-3/mo | >5 |
| 12 | 33 | engineer | 4 | N - 0 | different sports | <1 | 1-2/wk | 3 | none | 1 | 1-3/wk | 3-5 |
| 13 | 23 | industrial engineer | 3 | N - 0 | none | 0 | 0 | 2 | dinner | >3 | 1-3/mo | >5 |
| 14 | 38 | administrative | 3 | Y - 2 | aerobics | <1 | 1 | 2 | dinner | 2 | <1/mo | >5 |

* Education: 0, primary education; 1, higher education; 2, diploma; 3, bachelor's degree; 4, master's degree; 5, post-graduate level

[x] Smoker: Y, yes; N, no; 0, no smoker; 1, cigarettes; 2, shisha/hooka; 3, cigarettes and hooka

[‡] One cup equates to approximately 175 mL.

FIG 2 potted data feature individual data points
the mean percentage change and the ± standard deviation potted data feature individual data points the mean percentage change and the ± standard deviation potted data feature individual data points the mean percentage change and the ± standard deviation potted data feature individual data points the mean percentage change and the ± standard deviation potted data feature individual data points
the mean percentage change and the ± standard deviation potted data feature individual data points
the mean percentage change and the ± standard deviation potted data feature individual data points the mean percentage change and the ± standard deviation

BEVERAGE COMPOSITION CONTAINING EXTRACTS OF CAROB, ANISE, EUCALYPTUS AND/OR THYME

FIELD OF THE INVENTION

The subject matter described herein relates generally to tea compositions. More particularly, the present invention is directed toward tea compositions which provide numerous health and longevity benefits when consumed.

BACKGROUND OF THE RELATED ART AND THE INVENTION

Beverages in form of Tea have been a popular choice since time immemorial. People around the world have been consuming tea since thousands of years. Many cultures have a tradition of consuming tea for numerous reasons related to health and wellbeing. Tea is also considered to be a refreshing drink that can be served either hot or cold. Likewise, tea has been consumed to promote health and well-being.

For myriad reasons, including changes in diet and lifestyle, there has been a substantial increase in people suffering from health problems, such as cardiovascular diseases, hypertension, obesity, metabolic diseases and others. The widespread nature of these health issues has led to the necessity for expensive medical treatments, decrease in longevity and virility, mental health issues and numerous related problems.

In one of the relevant arts, US20140295049A1, a tea bag or a fiber-web made of non-soluble tea particles impregnated with soluble tea portion is disclosed.

Another relevant art, US20160255854A1, the composition of plant materials are contacted with a solvent to remove an extract. The remaining plant materials are then formed into a fibrous structure or network, such as a sheet or fibrous layer. The extract is concentrated and then reapplied to the plant materials. A resulting sheet or layer is then reduced to discrete pieces having a unique particle size distribution. A composition is produced that has a minimal fines and dust and has a relatively low bulk density.

Another relevant art, US20140234488A1, discloses a beverage system having a beverage, with at least one liquid. The variety of beverage is created including tea drink, coffee drink, milk drink, yogurt drink, malted drink, roasted cereal grain beverage, roasted nut and seed beverage, roasted bean beverage, distilled water, mineral water, sports drink, fruit juice, vegetable juice, fruit drink, vegetable drink, fruit skin drink, vegetable skin drink, plant drink, soft drink, alcoholic drink, and soup drink. The beverage may include flavoring ingredient, nutritional ingredient, health ingredient, and another ingredient. The beverage system is created in various form, including bubble beverage, instant beverage, and beverage with dissolved gas.

Another relevant art, CN104305394A, discloses a beverage system which produces instant drink comprising bubbles and dissolved gas. The drink system comprises liquid drink made into the following types: tea drink, coffee drink, milk beverage, yoghourt drink, malt drink, roasted grain drink, roasted nut and seed drink, roasted bean drink, distilled water, alkaline mineral water, sports drink, fruit juice, vegetable juice, fruit juice drink, vegetable drink, peel drink, vegetable peel drink, plant drink, soft drink, alcohol drink and soup drink. The drink can be manufactured by adding or not adding ingredients, comprising condiment components, nutritional ingredients, healthy components and other ingredients. The drink can be a hot drink, cold drink, ice drink and warm drink. The drink can contain caffeine or does not contain caffeine and is divided into diet types and non-diet types. The liquid comprises water, oil and alcohol. The drink system performs manufacturing in multiple forms such as bubble drinks, instant drinks and drinks with dissolved gas.

Another relevant art, US20090041914A1A discloses a beverage composition including water, milk solids, a tea material, and a pH buffer that includes a lactate salt and a carbonate salt. The pH buffer reduces or eliminates precipitation of milk protein when dissolved milk solids are mixed with acidic tea components.

Another relevant art, US20210100261A1 discloses a beverage composition that includes tea leaves, organic roasted dandelion root, organic cocoa shell, organic cardamom seed, organic ginger root, organic clove bud, organic black pepper, organic Ceylon cinnamon, peppermint, chicory root, orange peel, Manuka honey, lemon concentrate, and branch chain amino acids.

Another relevant prior art, WO2019040101A1, discloses a frozen tea or tonic composition including a mixture including at least two frozen ingredients selected from the group consisting of tea leaves, roots, herbs, fruit, flowers, vegetables, and combinations thereof, wherein each ingredient is not dried and is at least one of whole, unrefined, and unprocessed, the composition further characterized by an absence of added sugar, artificial ingredients, and artificial preservatives. The mixture defines a solid three-dimensional shape having an external surface area-to-volume ratio of at least 2/cm.

Most prior arts present a composition which is highly processed or comprises additional artificial additives. Therefore, to reap the benefits of a natural herbal tea it is essential to have a perfect composition curated with an expert knowledge, comprising ingredients in a form that may be easily brewed and consumable. More importantly, there is a need for a cost-effective tea beverage composition that could be consumed without any risk of side effects, and which may help to mitigate and/or prevents various health problems and promotes health and well-being in general.

SUMMARY OF THE INVENTION

In view of the deficiencies of the prior art, the objective of the present invention is to provide a tea composition comprising (including consisting essentially of or consisting of) carob, anise, eucalyptus, honey, thyme, and/or curcumin and/or water which may be effective in normalizing the parameters related to prediabetes and metabolic syndrome when consumed regularly.

Another objective of the present invention is to provide tea composition comprising (including consisting essentially of or consisting of) carob, anise, eucalyptus, thyme, and/or water which may be toxically safe and healthy.

In an embodiment, including but not limited to beverages or tea can be prepared to comprise 15% tea solids and 85% water. In other preferred embodiments, the compositions would consist of only tea solids or tea bags, as described further herein.

In an embodiment, the tea solids composition and water composition of the preferred embodiments can vary, including without limitation in the proportions as discussed further in relation to the various embodiments.

In an embodiment, the tea solids composition may comprise honey. In an embodiment, the type of honey used is manuka honey.

In an embodiment, the tea solids composition may comprise micellized curcumin which may be in liquid form or powdered form.

In an embodiment, the tea solids composition may comprise approximately 24% carob, 4% anise, 29% eucalyptus and 40% thyme.

In an embodiment, the tea solids composition may comprise approximately 25% carob, 5% anise, 30% eucalyptus and about 40% thyme.

In an embodiment, the tea solids composition may comprise approximately 24% carob, 4% anise, 29% eucalyptus, 40% thyme and 3% honey. In an embodiment, any type and form of honey may be used such as, but not limited to, Manuka honey.

In an embodiment, the tea solids composition may comprise approximately 23% carob, 4% anise, 28% eucalyptus, 39% thyme, 3% green tea and 3% honey. In an embodiment, any type and form of honey may be used such as, but not limited to, Manuka honey.

In an embodiment, the tea solids composition may comprise approximately 23% carob, 4% anise, 28% eucalyptus, 39% thyme, 3% green tea and 3% honey. In an embodiment, any type and form of honey may be used such as, but not limited to, Manuka honey.

In an embodiment, the tea solids in a preferred composition may be added to a prescribed quantity of distilled water and boiled for prescribed time duration such as approx. 5 minutes and brewed for approximate time duration of 3 minutes. The infusion may be filtered and cooled for a time duration of 30 min and decanted into a container to prepare the tea beverage.

In an embodiment, a pre-defined quantity of liquid curcumin formulation may be added to the prepared tea beverage. In an embodiment, micellized curcumin may be used. In an embodiment, the curcumin is in powdered or liquid form.

In an embodiment, the curcumin formulation may comprise of curcumin, desmethoxycurcumin, and bis-desmethoxycurcumin.

In an embodiment, the proportions of tea solids can be varied (up or down) by 25% or more to adjust and/or maximize the noted benefits, including without limitation health benefits and overall taste. Likewise, additional ingredients can be added, including without limitation, sweeteners, green tea, manuka honey and other herbs and natural ingredients.

In an embodiment, the water used in the tea beverage may be distilled water, tap water or a mineralized water.

In an embodiment, the components of the tea solids may be grown, harvested, processed and dried. In an embodiment, one or more of ingredients of the tea solids may be in form of micronized powder, or tea cut or in whole form.

In an embodiment, one or more of ingredients of the tea solids may be reduced to an average tea solid particles through means including, but not limited to, mechanical means such as milling and grinding, and then packaged and sold.

In an embodiment, the tea solids may be added to the boiled water directly or may be enclosed in tea bags.

In an embodiment, the tea solids may be placed into tea bag filter paper and sealed, either manually or by packaging machinery.

In an embodiment, the tea beverages may be prepared from the tea solids being exposed to hot or boiling water and steeped to taste and then packaged.

The present invention achieves each of the above-stated objectives and overcomes the foregoing disadvantages and problems. These and other objectives and other features and advantages of the invention will be apparent from the detailed description, referring to the attached drawings, and from the claims. Thus, other aspects of the invention are described in the following disclosure and are within the ambit of the invention.

BRIEF DESCRIPTION OF THE DRAWINGS

An exemplary embodiment of the present invention is illustrated by way of example in the accompanying drawings in which like reference numbers indicate the same or similar elements in which:

FIG. 1 shows a table listing the ingredients and their composition present in one serving of a tea beverage, according to an embodiment of the present invention.

FIG. 2 shows a table listing demographics of 29 volunteers for the experimental study conducted, according to an embodiment of the present invention.

DETAILED DESCRIPTION OF THE INVENTION

Figure 3:
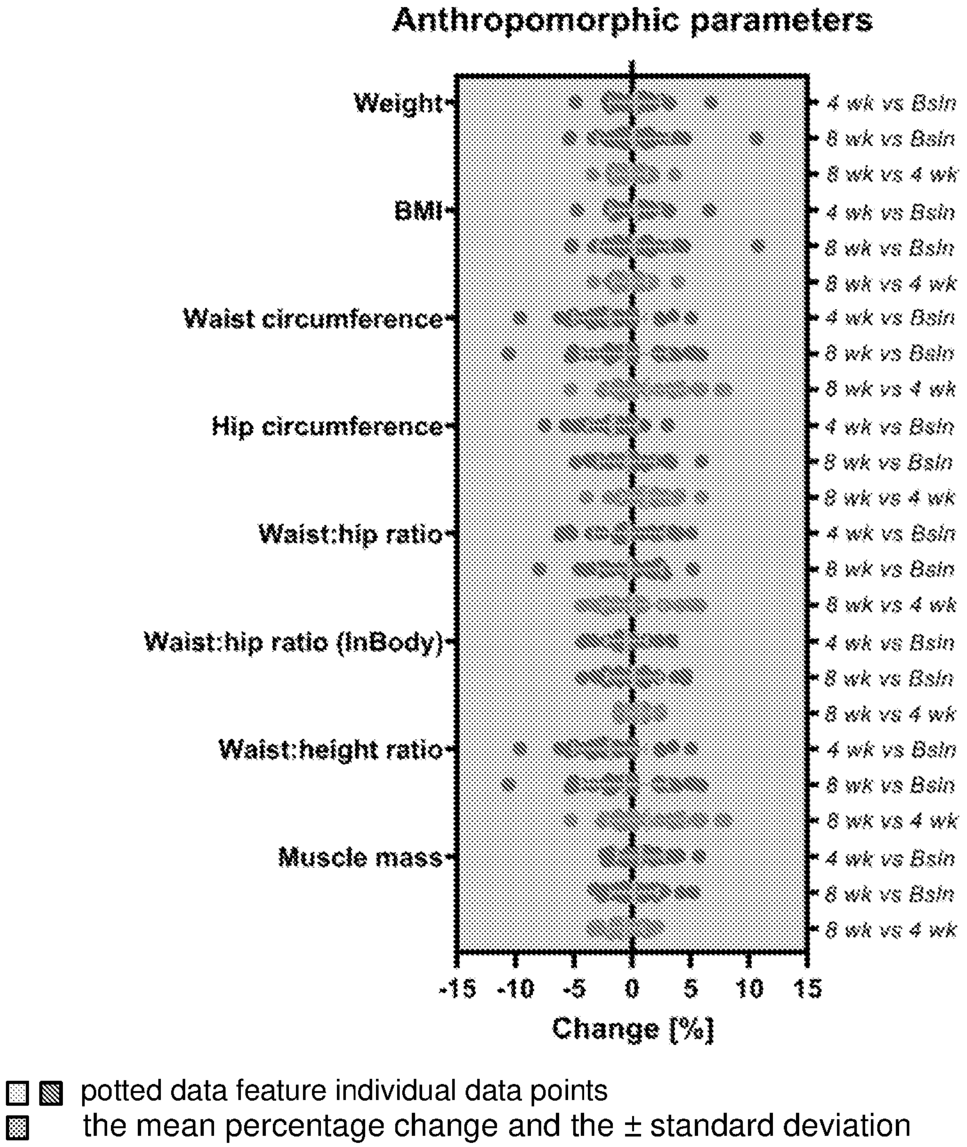
FIG. 3 shows a forest plot depicting anthropomorphic parameters with x-axis representing a percentage change in anthropomorphic parameters over time (left y-axis) following twice daily intake of the tea beverage, according to an embodiment of the present invention.

The embodiments herein and the various features and advantageous details thereof are explained more fully with reference to the non-limiting embodiments that are illustrated in the accompanying drawings and detailed in the following description. Descriptions of well-known components and processing techniques are omitted so as to not unnecessarily obscure the embodiments herein. The description used herein are intended merely to facilitate an understanding of ways in which the embodiments herein may be practiced and to further enable those of skill in the art to practice the embodiments herein. Accordingly, the description or explanation should not be construed as limiting the scope of the embodiments herein.

Various modifications to the disclosed embodiments will be readily apparent to those skilled in the art, and the general principles defined herein may be applied to other embodiments and applications without departing from the spirit and scope of the present invention. Thus, the present invention is not limited to the embodiments shown but is to be accorded the widest scope consistent with the claims. The terms like can be, shall be, could be, and other related terms herein disclosed in the foregoing and later parts of the specification in any means do not limit or alter the scope of the present invention. The terms are provided just for the mere understanding of the main invention and its embodiments.

Exemplary embodiments are described with reference to the accompanying drawings. Wherever convenient, the same reference numbers are used throughout the drawings to refer to the same or like parts. While examples and features of disclosed principles are described herein, modifications, adaptations, and other implementations are possible without departing from the spirit and scope of the disclosed embodiments.

As used herein, the term "comprising" also encompasses "consisting of" and "consisting essentially of". Likewise, the term "comprises" also encompasses "consists of" and "consists essentially of."

Except where mutually exclusive, any feature described herein may be applied to any aspect of the invention and/or combined with any other feature(s) described herein.

As used herein, the term "beverage" refers to a substantially aqueous drinkable composition suitable for human consumption, including without limitation, ready-to-drink packaged beverages that are sold in prepared form and are ready for human consumption. In at least one preferred embodiment, such a beverage comprises at least 85% water by weight.

As used herein, the term "tea solids" refers to the leaves, seeds, stems, twigs, vines, pods and/or other parts of carob, anise, eucalyptus, thyme, black tea and green tea plants in any form, including without limitation to whole tea solids, loose-leaf tea, ground tea solids and tea solids in powder and micronized powder form. Tea in powder form is easier to handle in transit for example in delivery and shipping.

As used herein, the term "tea bag" refers to a porous sachet or similar container which contains tea leaves or powdered tea, in a manner that when immersed in a liquid such as water the tea leaves diffuse to make into a beverage in a contained manner.

Tea beverages, tea solids and tea according to the invention described herein involve decoction of a single ingredient or a blend of various ingredients such as but not limited to, carob, anise, eucalyptus, thyme and water. Some blends may also include additional natural ingredients.

The ingredient carob referred herein, is a legume that is high in fiber, low in fat, caffeine-free and a good source of antioxidants. The carob increases satiety and serves as a low-glycemic index ingredient, thereby controlling the glycemic response after intake while conferring sweetness to the tea. Moreover, long-term consumption of carob improves lipid oxidation and postprandial insulin sensitivity in healthy individuals and lowers total cholesterol and low-density lipoprotein (LDL) in hypercholesterolemic subjects. Hence, it is useful in controlling diabetes, lowering cholesterol levels and promoting weight loss.

The ingredient anise referred herein, is an herb that contains thymol, terpineol and anethole, and is beneficial in treating many health issues, including the flu, coughs and colds, female menstruation, male menopause, lack of sex drive, lack of appetite, insomnia, asthma and other problems.

The ingredient eucalyptus referred herein, is a tree, whose leaves and oil are used to make medicine. Eucalyptus has been reported to possess antioxidant, anti-inflammatory, antimicrobial, and potentially antidiabetic properties. It is beneficial for health problems, including asthma, bronchitis, diabetes, liver and gall bladder issues, dental plaque, gingivitis, bad breath and headaches.

The ingredient thyme referred herein, is an herb. Its flower, leaves and oil are used in dietary as well as medicinal purposes. Thyme extract contains compounds which have antioxidant, anti-inflammatory, antimicrobial, and antitussive properties. It has antibacterial, insecticidal and antifungal properties, and has numerous vitamins and minerals. Thyme is beneficial in treating a variety of health problems, including bacterial infections, fungal infections. It is said to control blood pressure, boost immunity, boost mood and provide a pleasant aroma and flavor for food and beverages.

The ingredient green tea extract or leaves are made from *Camellia sinensis* leaves and contain polyphenols and catechins that are known to promote health and provide numerous benefits, including promoting healthy brain function, preventing cell damage, reducing the risk of certain cancers, antibacterial properties and reduces the risk of diabetes heart disease and high blood pressure.

The ingredient, manuka honey referred herein, is a honey made by bees that pollinate the *Leptospermum scoparium* bush (also known as a tea tree). Manuka honey is an antibacterial, antiviral and anti-inflammatory. It has antioxidant health benefits, and is used to promote the healing of wounds, oral health, soothe sore throats, aid in digestive issues, helps prevent ulcers, acne and other skin ailments. In an embodiment, any variety or form of honey may be used. In an embodiment, any type and form of honey may be used.

The ingredient, water soluble curcumin, is a phytochemical derived from the roots of the *Curcuma longa* plant. The dried and ground roots of *Curcuma longa* plant are commonly known as turmeric. Curcumin is a bioactive compound which is 2-3% of turmeric. Curcumin has widespread use as a food supplement with clinically proven health benefits. Studies have demonstrated that the compound is effective in reducing inflammation in patients with osteoarthritis, and rheumatoid arthritis, ulcerative colitis and psoriasis. Curcumin acts as an anti-oxidant that neutralizes free radicals in the body that form during mild and chronic inflammation. Curcumin is also beneficial in treatment of metabolic syndrome, promoting a reduction in blood cholesterol, low-density lipoprotein (LDL), serum triglycerides as well as liver fat. Through its lowering action on free fatty acids in the blood, the compound has been shown to exert a glucose-lowering effect in diabetics and prevented prediabetics from developing type 2 diabetes. Studies show that athletes experience better recovery when using curcumin after strenuous exercise. The compound is effective against certain forms of pain and ameliorates anxiety and feelings of depression. Owing to its effects on blood coagulation and fibrinolysis, curcumin is a blood thinner (just like aspirin), which can be advantageous to patients who suffer from certain cardiovascular diseases.

The present invention relates to tea beverages which is a nutritional supplement. The tea solid comprising carob, anise, eucalyptus, thyme, honey, curcumin are enclosed in tea bags and dissolved or infused in water for a tea beverage. Curcumin used may be water soluble curcumin or micellized curcumin or powdered curcumin. Additional natural ingredients such as green tea, manuka honey, black tea and other herbs may be added. The medicinal properties of the nutritional supplement and tea ingredients favorably modulate physiological and biochemical processes in the body that lead to improved longevity, vitality, and psychological well-being.

The disclosed subject matter can be described in more detail with reference to the following Examples. These Examples include some, but not all, embodiments of the disclosed subject matter described herein. For the sake of clarity, the present invention may be embodied in various forms. Accordingly, the specific details disclosed herein are not to be interpreted as limiting the scope of the invention, but rather as a basis for the claims and for teaching one skilled in the art to practice the invention in any appropriate manner, structure or system.

In an embodiment, the composition comprises about 15% tea solids and about 85% water. In other preferred embodiments, the compositions would consist of only tea solids or tea bags, as described further herein.

The tea solids portion of the preferred embodiments can vary, including without limitation in the proportions noted below:

In an embodiment, the composition comprises tea solids with about 25% carob, about 5% anise, about 30% eucalyptus and about 40% thyme.

In an embodiment, the composition comprises tea solids with about 24% carob, about 4% anise, about 29% eucalyptus, about 39% thyme and about 4% green tea.

In an embodiment, the composition comprises tea solids with about 24% carob, about 4% anise, about 29% eucalyptus, about 40% thyme and about 3% honey. In an embodiment, any type and form of honey may be used such as, but not limited to, Manuka honey In an embodiment, the composition comprises tea solids with about 23% carob, about 4% anise, about 28% eucalyptus, about 39% thyme, about 3% green tea and about 3% honey. In an embodiment, any type and form of honey may be used such as, but not limited to, Manuka honey.

In other preferred embodiments, the proportions of tea solids can be varied (up or down) by 25% or more to adjust and/or maximize the noted benefits, including without limitation health benefits and overall taste. Likewise, additional ingredients can be added, including without limitation, sweeteners, black tea and other natural ingredients.

The following Examples have been included to provide guidance to one of ordinary skill in the art to practice representative embodiments of the disclosed subject matter.

Example 1: This is a representative procedure for preparing all-natural healthy tea, according to the following proportions: 15% tea solids and 85% water. The tea solids portion of one of the preferred embodiments would be in the following proportions: 25% carob; 5% anise; 30% eucalyptus; and 40% thyme. The procedure described can be used to make small batches or large batches, in the proportions indicated above. Tea beverages, tea solids and tea bags have been made for thousands of years. While the methods can vary, they all involve the key common elements. The components of the tea solids are grown, harvested, processed and dried. In an embodiment the tea solids may be in form of micronized powder, the average tea solids' particles are reduced through means including, but not limited to, mechanical means such as milling and grinding, and packaged so that they can be easily transited by shipping or delivered by loading on a vehicle and sold in the market.

For tea bags, the tea solids are processed to convert the tea solids into tea cut shape and size and then placed into tea bag filter paper and sealed, either manually or by machinery. For tea beverages, the tea solids or tea bags are exposed to hot or boiling water and steeped to taste, and then packaged.

Example 2: This is a representative procedure for preparing all-natural healthy tea, according to the following proportions: 15% tea solids and 85% water. The tea solids portion of one of the preferred embodiments would be in the following proportions: 24% carob; 4% anise; 29% eucalyptus; 39% thyme; and 4% green tea. The procedure of Example 1 can be used to make the beverages, tea solids and tea bags.

Example 3: This is a representative procedure for preparing all-natural healthy tea, according to the following proportions: 15% tea solids and 85% water. The tea solids portion of one of the preferred embodiments would be in the following proportions: 24% carob; 4% anise; 29% eucalyptus; 40% thyme; and 3% honey. In an embodiment, any type and form of honey may be used such as, but not limited to, Manuka honey. The procedure of Example 1 can be used to make the beverages, tea solids and tea bags.

Example 4: This is a representative procedure for preparing all-natural healthy tea, according to the following proportions: 15% tea solids and 85% water. The tea solids portion of one of the preferred embodiments would be in the following proportions: 23% carob; 4% anise; 28% eucalyptus; 39% thyme; 3% green tea; and 3% honey. In an embodiment, any type and form of honey may be used such as, but not limited to, Manuka honey. The procedure of Example 1 can be used to make the beverages, tea solids and tea bags.

Example 5: This is a representative procedure for preparing all-natural healthy tea, according to the following steps: adding 350 g of anise, 70 g of cut carob pots, 52.5 g of thyme, 35 g of eucalyptus, and 252 g of honey to 6.5 liter of distilled water. Boiling the mixture for 5 minutes and brewing for 3 minutes. Filtering the brewed infusion and cooling for 30 minutes. The tea is then decanted into a cup of 175 ml. In an embodiment, a single serving of the tea beverage may be of 175 ml in quantity. In an embodiment, 10 drops of proprietary liquid curcumin formulation is added to the cup of tea. In an embodiment, the curcumin formulation comprises of curcumin, desmethoxycurcumin, and bis-desmethoxycurcumin. In an embodiment, any type and form of honey may be used such as, but not limited to, Manuka honey. In an embodiment, micellized curcumin may be used. In an embodiment, curcumin may be in liquid or powdered form.

FIG. 1 shows a table listing the ingredients and their composition present in one serving of a tea beverage, according to an embodiment of the present invention. The tea beverage of 175 ml forms for a single serving which is recommended to be consumed twice per day. In an experimental study conducted, two servings of the tea prepared using the preferred methodology is served to the 29 volunteers (15 male and 14 female) of age in the range defined as 34±6 and 36±9 years (mean± standard deviation (SD)) for time duration of 8 weeks.

FIG. 2 shows a table listing demographics of 29 volunteers for the experimental study conducted, according to an embodiment of the present invention. The table of FIG. 2 also provides the normal ranges for each parameter along with a general description and relevance in health and disease.

In the experimental study conducted, each participant was tested for 52 parameters after an overnight fast. The physiological parameters tested are related to cardiovascular, hematological, metabolic and endocrinological (sub stratified into general, carbohydrates, lipids, and vitamins), urine markers, organ function and tissue damage markers, and inflammation markers. The test being conducted at a duration of 4 weeks and 8 weeks for each participant. All procedures were conducted by a board-certified physicians and registered nurses.

The results of the tests were analyzed as per null hypothesis significance testing by considering a P-value of ≤0.05 statistically significant.

FIG. 3 is a forest plot depicting anthropomorphic parameters with x-axis representing a percentage change in anthropomorphic parameters over time (left y-axis) following twice daily intake of tea, according to an embodiment of the present invention. The periods compared are provided on the right y-axis. Plotted data feature individual data points, the mean percentage change (central vertical grey line), and the ± standard deviation (lateral grey vertical lines). Statistically significant changes are indicated by an increase or decrease in highlight of the periods compared on the right y-axis. The absence of such highlights means that there were no statistically significant differences between the 2 periods compared, and that therefore the values did not change over the respective time frame. As mentioned in the forest plot shown in FIG. 3, the terms "BMI" represents body mass index, "wk" represents weeks and "Bsln" represents baseline (day 0 measurement).

Figure 4:
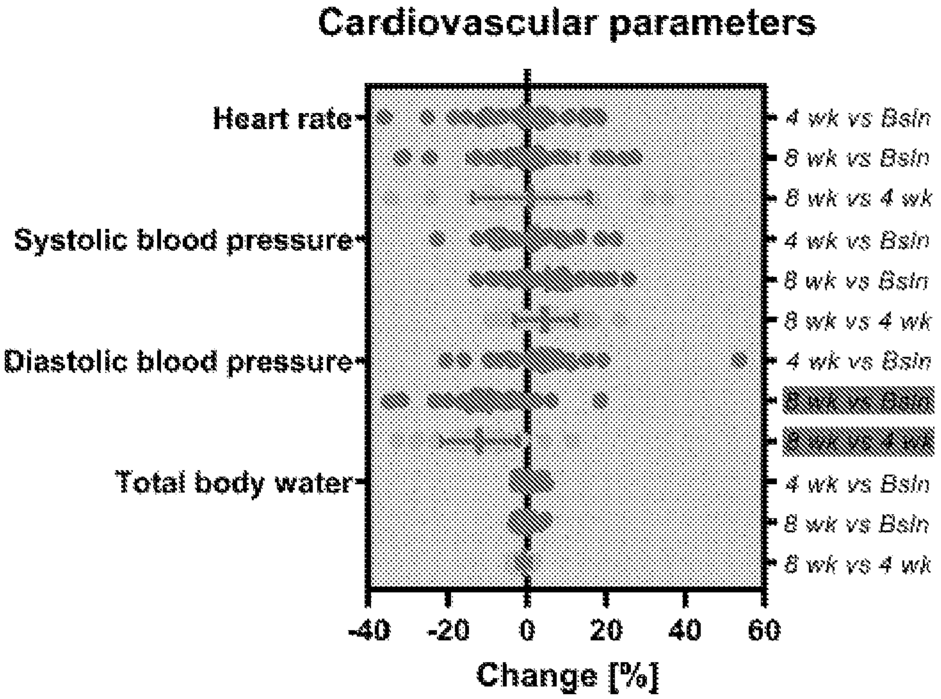
FIG. 4 shows a forest plot depicting a percentage change (x-axis) in cardiovascular parameters over time (left y-axis) following twice daily intake of tea, according to an embodiment of the present invention.

FIG. 4 is a forest plot depicting a percentage change (x-axis) in cardiovascular parameters over time (left y-axis) following twice daily intake of tea, according to an embodiment of the present invention. The periods compared are provided on the right y-axis. Plotted data feature individual data points, the mean percentage change, and the ± standard deviation. Statistically significant changes are indicated by an increase or decrease of highlights of the periods compared on the right y-axis. The absence of such highlights means that there were no statistically significant differences between the 2 periods compared, and that therefore the values did not change over the respective time frame. As mentioned in the forest plot shown in FIG. 4, the terms "wk" represents weeks and "Bsln" represents baseline (day 0 measurement).

Figure 5:
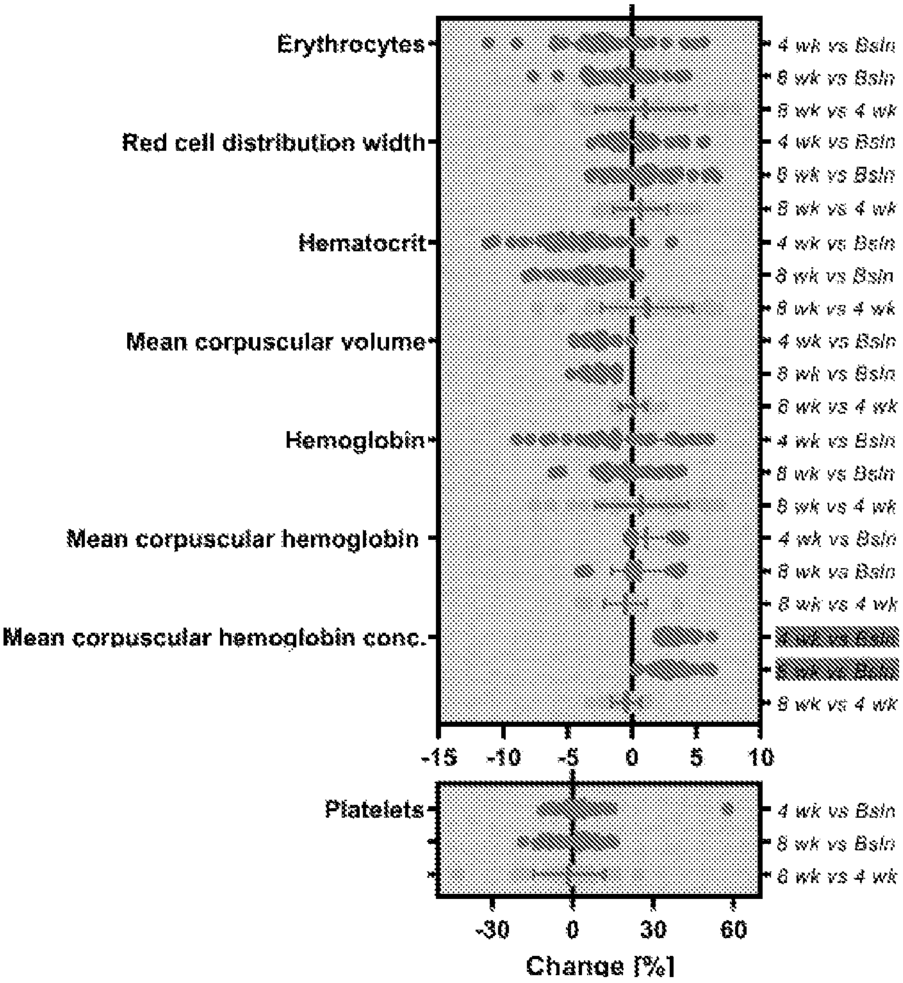
FIG. 5 shows a forest plot depicting a percentage change (x-axis) in hematological parameters (left y-axis) over time following twice daily intake of tea, according to an embodiment of the present invention.

FIG. 5 is a forest plot depicting a percentage change (x-axis) in hematological parameters (left y-axis) over time following twice daily intake of tea, according to an embodiment of the present invention. The periods compared are provided on the right y-axis. Plotted data feature individual data points, the mean percentage change, and the ± standard deviation. Statistically significant changes are indicated by an increase or decrease of highlights of the periods compared on the right y-axis. The absence of such highlights means that there were no statistically significant differences between the 2 periods compared, and that therefore the values did not change over the respective time frame. As mentioned in the forest plot shown in FIG. 5, the terms "conc." represents concentration, "wk" represents weeks and "Bsln" represents baseline (day 0 measurement).

Figure 6:
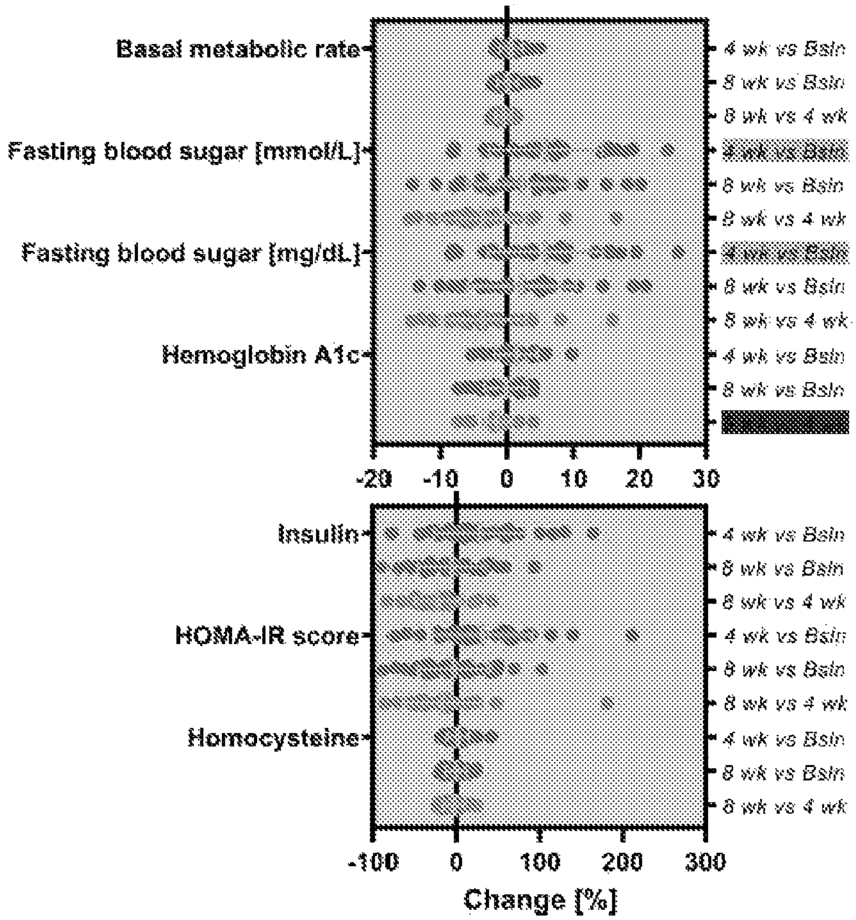
FIG. 6 shows a forest plot depicting a percentage change (x-axis) in metabolic and endocrinological (general, carbohydrates, and vitamins) parameters (left y-axis) over time following twice daily intake of tea, according to an embodiment of the present invention.

FIG. 6 is a forest plot depicting a percentage change (x-axis) in metabolic and endocrinological (general, carbohydrates, and vitamins) parameters (left y-axis) over time following twice daily intake of tea, according to an embodiment of the present invention. The periods compared are provided on the right y-axis. Plotted data feature individual data points, the mean percentage change, and the ± standard deviation. Statistically significant changes are indicated by an increase or decrease of highlights of the periods compared on the right y-axis. The absence of such highlights means that there were no statistically significant differences between the 2 periods compared, and that therefore the values did not change over the respective time frame. As mentioned in the forest plot shown in FIG. 6, the terms "HOMA-IR" represents homeostatic model assessment of insulin resistance, "wk" represents weeks and "Bsln" represents baseline (day 0 measurement).

Figure 7:
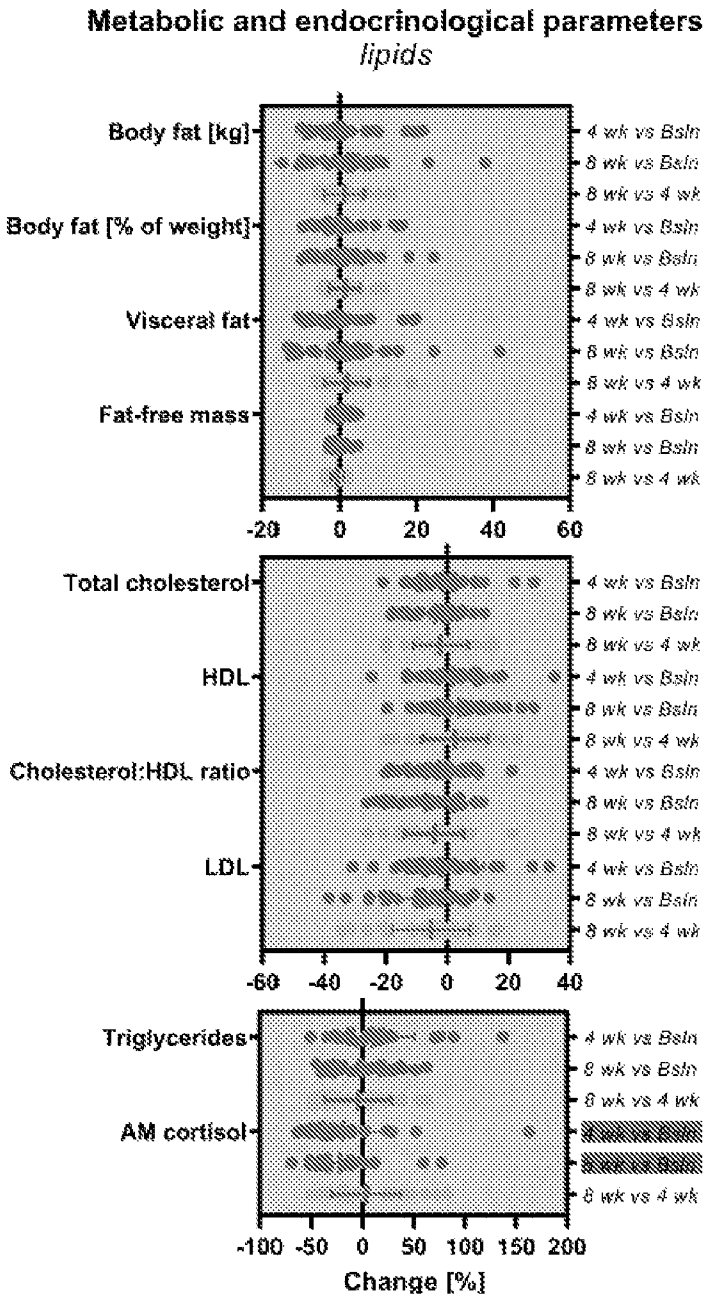
FIG. 7 shows a forest plot representing a percentage change (x-axis) in metabolic and endocrinological (lipids) parameters (left y-axis) over time following twice daily intake of tea, according to an embodiment of the present invention.

FIG. 7 shows a forest plot representing a percentage change (x-axis) in metabolic and endocrinological (lipids) parameters (left y-axis) over time following twice daily intake of tea, according to an embodiment of the present invention. The periods compared are provided on the right y-axis. Plotted data feature individual data points, the mean percentage change, and the ± standard deviation. Statistically significant changes are indicated by an increase or decrease of highlights of the periods compared on the right y-axis. The absence of such highlights means that there were no statistically significant differences between the 2 periods compared, and that therefore the values did not change over the respective time frame. As mentioned in the forest plot shown in FIG. 7, the term "HDL" represents high-density lipoprotein (good cholesterol), "LDL" represents low-density cholesterol (bad cholesterol); "wk" represents weeks and "Bsln" represents baseline (day 0 measurement).

Figure 8:
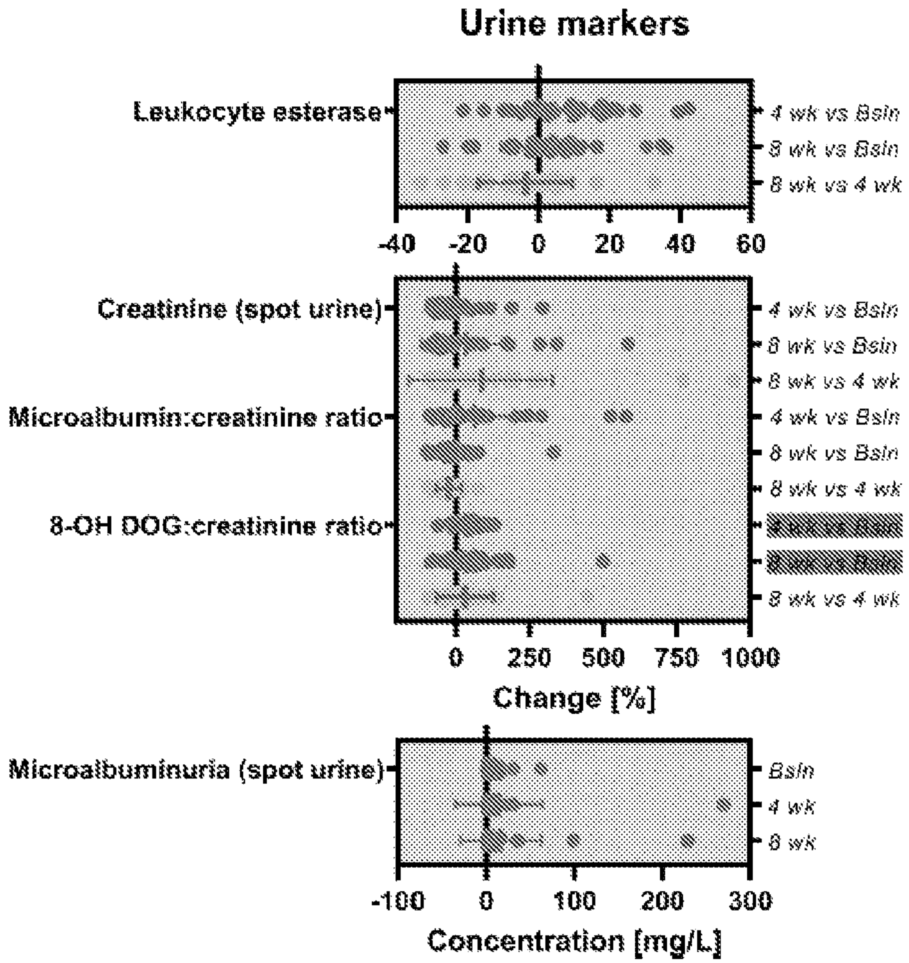
FIG. 8 shows a forest plot representing a percentage change (x-axis) in urine markers (left y-axis) over time following twice daily intake of tea, according to an embodiment of the present invention.

FIG. 8 shows a forest plot representing a percentage change (x-axis) in urine markers (left y-axis) over time following twice daily intake of tea, according to an embodiment of the present invention. The periods compared are provided on the right y-axis. Plotted data feature individual data points, the mean percentage change, and the ± standard deviation. Statistically significant changes are indicated by an increase or decrease of highlights of the periods compared on the right y-axis. The absence of such highlights means that there were no statistically significant differences between the 2 periods compared, and that therefore the values did not change over the respective time frame. As mentioned in the forest plot shown in FIG. 8, the term "8-OH DOG" represents "8-hydroxy-2'" represents-deoxyguanosine, "wk" represents weeks and "Bsln" represents baseline (day 0 measurement).

Figure 9:
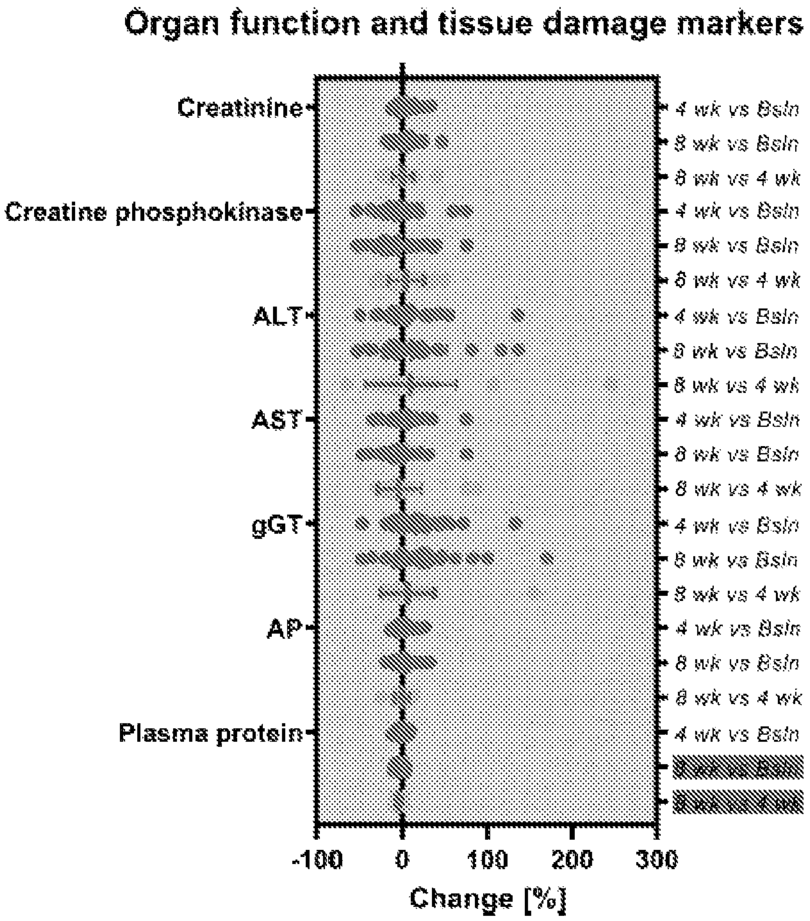
FIG. 9 shows a forest plot of the percentage change (x-axis) in organ function and tissue damage markers (left y-axis) over time following twice daily intake of the tea beverage.

FIG. 9 shows a forest plot of the percentage change (x-axis) in organ function and tissue damage markers (left y-axis) over time following twice daily intake of the tea beverage. The periods compared are provided on the right y-axis. Plotted data feature individual data points, the mean percentage change, and the ± standard deviation. Statistically significant changes are indicated by an increase or decrease of highlights of the periods compared on the right y-axis. The absence of such highlights means that there were no statistically significant differences between the 2 periods compared, and that therefore the values did not change over the respective time frame. As mentioned in the forest plot shown in FIG. 9, the term "ALT" represents alanine aminotransferase, "AST" represents aspartate aminotransferase, "gGT" represents gamma glutamyl transpeptidase, "AP" represents alkaline phosphatase, "wk" represents weeks and "Bsln" represents baseline (day 0 measurement).

Figure 10:
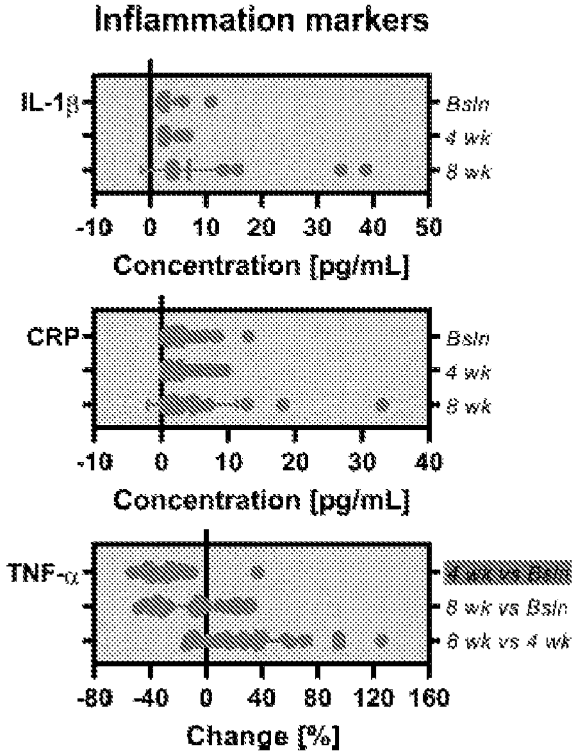
FIG. 10 shows a forest plot of the percentage change (x-axis) in inflammation markers (left y-axis) over time following twice daily intake of the tea beverage.

FIG. 10 shows a forest plot of the percentage change (x-axis) in inflammation markers (left y-axis) over time following twice daily intake of the tea beverage. The periods compared are provided on the right y-axis. Plotted data feature individual data points, the mean percentage change, and the ± standard deviation. Statistically significant changes are indicated by an increase or decrease of highlights of the periods compared on the right y-axis. The absence of such highlights means that there were no statistically significant differences between the 2 periods compared, and that therefore the values did not change over the respective time frame. As mentioned in the forest plot shown in FIG. 10, the term "IL-1β" represents interleukin 1 beta, "CRP" represents C-reactive protein, "TNF-α" represents tumor necrosis factor-alpha, "wk" represents weeks and "Bsln" represents baseline (day 0 measurement).

In an embodiment, the volunteers selected for the study may be overweight and who presented prediabetes and symptoms related to metabolic syndrome. Since metabolic syndrome harnesses at least three of the five following medical conditions simultaneously: abdominal obesity, high blood sugar, high serum triglycerides, low serum high-density lipoprotein (HDL), and high blood pressure. The result of the study may help determine an objective measure of efficacy of the tea in combatting the symptoms of prediabetes and metabolic diseases.

On the basis of the analysis of the results, it may be concluded that the baseline body mass index (BMI) of male participants was 26.1±3.5. The overweight BMI in men concurred with an above-normal body fat percentage (22.6±6.9%), a waist:hip ratio of 0.90±0.06 (signifying overweight), and a waist:height ratio of 0.53±0.06 (signals an increased medical risk) as shown in FIG. 6. Male participants were seen to have elevated levels of creatine phosphokinase (CPK; 116±46 U/L), which is a biomarker for obesity. Moreover, men had borderline high triglyceride levels (119±52 mg/dL) and low yet still acceptable HDL levels (42.4±7.5 mg/dL) that put them at an increased risk for cardiovascular disease. The male participants also presented with above-normal fasting insulin (10.9±10.8 μIU/mL) and insulin resistance score (2.2±2.2). These metabolic manifestations are inherent to the relationship between fat build-up and disrupted sugar metabolism. In response to enduring overnutrition and fat accumulation, the liver and other organs become less responsive to insulin and the body gradually develops insulin resistance. The pancreas, which produces insulin, attempts to counter the developing resistance by secreting more insulin into the blood. When increased blood insulin levels can no longer compensate for the impaired insulin response of all metabolic organs, including fat tissue, liver, muscle, pancreas, and even the central nervous system, type 2 diabetes develops. With increasing BMI, the HDL, serum triglycerides, and visceral fat would ultimately become abnormal and exacerbate the prediabetes and metabolic syndrome. It is therefore imperative that no further deterioration of health occurs, e.g., through lifestyle changes and/or nutritional support. Hyperhomocysteinemia (17.7±4.2) was found in men and indicates deficiency in vitamin B12, vitamin B6, and/or folic acid (vitamin B9). Elevated levels of homocysteine are most likely caused by improper diet and are also linked to heart and cerebrovascular disease. Furthermore, a state of low-grade inflammation was measured in overweight men. Tumor necrosis factor-α (TNF-α) was elevated (8.5±2.0 pg/mL) but interleukin 1β (IL-1β) and C-reactive protein (CRP) were in-range, making the inflammation low-grade. TNF-α is a pro-inflammatory cytokine that mediates systemic inflammation. This acute-phase protein is released by mainly innate immune cells called macrophages. In this particular cohort of participants, elevated TNF-α levels can be explained by two mechanisms. First, persistent hyperglycemia due to insulin resistance can lead to shedding of the endothelial glycocalyx, a protective layer covering the inner surface of almost all blood vessels. The shed glycocalyx constituents activate macrophages, which in turn release of TNF-α into the blood. Second and more important, the participants carried excessive body fat that is composed of several different cell types, including fat cells and macrophages that produce pro-inflammatory cytokines including TNF-α and interleukin 6 (IL-6, not measured in this study). The released TNF-α subsequently causes and exacerbates inflammation and insulin resistance. Finally, male participants exhibited below-normal serum creatinine levels (0.73±0.12 mg/dL), indicating good renal function despite the potentially deleterious effects of obesity on the kidneys.

The baseline BMI of the female participants was 26.9±3.9 as shown in table of FIG. 7. Overweight women presented with above-normal body fat percentage (39.2±6.4%) and visceral fat (135±39 cm2), a waist:hip ratio of 0.81±0.05, a waist:height ratio of 0.54±0.06, aberrant CPK levels (75±23 U/L), and near-borderline high triglyceride levels (112±51 mg/dL). Visceral fat is body fat that is stored within the abdominal cavity around internal organs such as the liver, pancreas, and intestines, affecting their function. Visceral fat in itself augments insulin resistance. Correspondingly, overweight female participants exhibited problematic sugar metabolism, as evidenced by elevated fasting insulin levels (9.9±6.3 μIU/mL) and insulin resistance scores (2.0±1.4). In addition to having elevated levels of TNF-α (9.5±2.7 pg/mL) in the blood, the included women also expressed abnormally high levels of CRP (4.1±3.5 mg/L), underpinning their low-grade inflammatory state. As TNF-α, CRP is an acute phase protein whose blood concentration rises in response to inflammatory signaling mediated by macrophage- and fat cell-derived IL-6. CRP is synthesized in the liver and its production is stimulated by biochemical factors (adipokines) released from macrophages and fat cells. People who are overweight and obese possess so-called overweight/obese white adipose tissue. The expansion of white adipose tissue in overweight and obese individuals leads to mechanical and cellular stress in fat cells, resulting in the release of free fatty acids such as triglycerides and inflammatory cytokines. Various types of immune cells are subsequently recruited to the overweight/obese white adipose tissue, driving local and systemic inflammation. The general rule is that the more visceral fat (i.e., the higher the BMI), the greater the inflammatory response. Not only do the infiltrated macrophages locally produce TNF-α and IL-6 to propel an inflammatory state, but the IL-6 triggers the synthesis and release of CRP by the liver, further compounding the local and systemic inflammation and insulin resistance. Moreover, CRP is a strong independent predictor of incident diabetes and incident cardiovascular disease and is correlated with other elements of metabolic syndrome such as fasting insulin and microalbuminuria. Again, it is imperative to curtail further development of prediabetes and symptoms of metabolic syndrome t exercise, and effective dietary supplementation. In a comparative analysis, the female participants had in-range homocysteine levels in contrast to men and, in similarity to men, renal function was not perturbed (below-normal serum creatinine of 0.47±0.09 mg/dL).

On the basis of the analysis, conclusions can be drawn that given the plethora of physiology- and biochemistry-modulating properties of curcumin and other ingredients, a daily intake of the tea over the course of 8 weeks may lead to an improvement in parameters tied to mainly prediabetes and metabolic syndrome. As depicted in FIGS. 4-10, improvement and restoration of some of the parameters to normal levels can be seen. Also, it may be concluded that the majority of the aberrant parameters were connected to prediabetes and metabolic syndrome.

As depicted by FIGS. 3-10, daily consumption of tea resulted in the normalization of multiple outcome measures. When the entire study cohort is considered as a whole, a decrease in insulin resistance score, triglyceride levels, and homocysteine fell back to normal range after 8 weeks, while TNF-α declined to healthy levels after 4 weeks of tea intake. In the male cohort as shown in FIG. 6, the results were echoed with the exception of homocysteine, which remained high throughout the trial period. In the female cohort, as shown in FIG. 7, fasting insulin and insulin resistance score normalized after 8 weeks, which was preceded by normalization of TNF-α levels at the 4-weeks follow-up. Also, cortisol levels in women decreased to below the bottom reference limit. Since the participants were explicitly instructed not to change their lifestyle and daily routine, there is a high probability that the normalization of several key parameters is ascribable to the consumption of the tea. With the tea comprising multiple active principals with proven health benefits, it is impossible to accurately pinpoint the contribution of each ingredient. It is also possible that the ingredients collectively impart a non-linear effect (i.e., '1±1=3').

The most important result was the normalization of inflammatory markers (TNF-α in men and women and CRP in women) as shown in FIG. 10. The reduction in TNF-α is statistically significant in the overall cohort ($P<0.001$) and in the female participants ($P=0.01$). Chronic inflammation is a state that encompasses the non-stop activation of cells of the innate immune system (e.g., macrophages) and the corollary production and release of pro-inflammatory cytokines into inflamed tissue and the bloodstream. Chronic inflammation is deleterious to health in that it potentiates the development of cancer, cardiovascular disease, ageing, rheumatoid arthritis, type 2 diabetes, non-alcoholic fatty liver disease, asthma, and neurodegenerative diseases such as Alzheimer's. Controlling chronic inflammation is therefore key to a healthy life.

Furthermore, 4-week and 8-week consumption of the tea reduced circulating levels of cortisol ($P<0.045$) as seen in FIG. 7. Cortisol is a steroid hormone that is produced mainly by the kidneys' adrenal gland and released in response to stress and low blood glucose concentrations. Chronic exposure to elevated levels of the hormone promotes insulin resistance. Cortisol also modulates the immune system by preventing the release of substances that cause inflammation, including TNF-α, while at the same time making certain adaptive immune cells less amenable to pro-inflammatory ques and suppressing the activity and cytotoxic potential of natural killer cells. So, on the one hand cortisol works as an anti-inflammatory but on the other hand the hormone impairs our ability to fend off infections. Its control is therefore important in maintaining immune function and ameliorating the symptoms of prediabetes and metabolic syndrome. What is particularly striking is that the reduction in TNF-α as shown in FIG. 10, occurred concomitantly with lowered cortisol levels, which normally exist in an inverse relationship. These findings suggest that metabolic factors other than cortisol, probably primed by constituents of the tea, were responsible for the anti-inflammatory effects.

This study conducted provides a mechanistic insight into the pharmacology of the tea. This study was conducted to establish whether any physiological modulation could be achieved with consumption of the tea in order to promote health. It may be concluded that the consumption of tea can reduce symptoms of prediabetes and metabolic syndrome. Accordingly, it may be concluded that the consumption of tea is restorative as well as beneficial in preventing the further escalation of already out-of-balance medical conditions that could culminate in more profound insulin resistance, diabetes, and cardiovascular problems. It is expected that the daily intake of the tea with a good diet and exercise will expedite the restoration of an overweight body to metabolic normalcy.

As indicated in the previous section, cortisol is a stress hormone. Maladaptive cognitive responses to stress, such as magnification, rumination, and helplessness, may intensify cortisol release and with it forge a physiological stress response to psychological stress. Such a response is referred to as a psychosomatic reaction. The psychological stress is a relative concept that is subject to a person's perception of potential stressors and can therefore manifest even at basically inconsequential external stimuli such as an unpleasant co-worker's body odor, chaotic morning traffic, or adversity to certain sounds (misophonia). Failure to cope properly with stressors may lead to prolonged or exaggerated stress and exacerbation of the physiological response, namely sustained hypercortisolemia, which is detrimental to health. Results of the study, show that the regular consumption of tea significantly reduce cortisol levels thus show that the anxiolytic potency of the product and validates the result of the study.

A toxicological assessment performed using two distinct approaches. In the first approach, the urine markers and the organ function and tissue damage markers were evaluated, these being the most sensitive barometer for xenobiotic toxicity. Any changes compared to baseline measurements signal an adverse reaction or impaired organ function in response to daily tea consumption. As reported in FIGS. 8 and 9, the only marker that increased was the 8-hydroxy-2'-deoxyguanosine:creatinine ratio in spot urine, while the only marker that decreased was total protein a DNA breakdown product. This DNA oxidation metabolite is in fact part of normal cell metabolism, as its formation occurs at an average frequency of 2400 per cell. Once formed, the DNA damage is repaired and the 8-hydroxy-2'-deoxyguanosine is removed quickly via the renal system (elimination half-life is 11 min) and it ends up in urine. The presence of 8-hydroxy-2'-deoxyguanosine in urine signifies that radicals formed in our body have damaged nuclei, but in the wake of no apparent damage in organs/tissues (liver, biliary system, heart, kidneys, brain, muscle, blood cells), perturbed function (kidneys), and decreased inflammation as shown in FIG. 10, there is no reason to assume that the tea induced toxicity. Moreover, compared to baseline, the creatinine levels in urine had decreased at the 4-week and 8-week follow-up as shown in FIG. 5. Nevertheless, the lowering of creatinine levels may have skewed the 8-hydroxy-2'-deoxyguanosine: creatinine ratio in urine in favor of the former, which is standardly corrected for total creatinine. With respect to the hypoproteinemia, although protein levels dropped significantly at 8 weeks, these were still within normal range. This phenomenon, also in the context of the abovementioned reasons, therefore cannot be considered to reflect toxicity.

The second approach being, looking at parameters that were in normal range at the baseline measurement but became out of range at the follow-ups. As shown in table of FIG. 5, this was only noted for CRP (4.7±6.6 mg/L at 8 weeks versus 3.2±2.9 mg/L at baseline). The mean CRP level was elevated because of 3 outliers as shown in FIG. 10, which is also reflected by the high standard deviation. In this instance the elevated CRP can be dismissed as a general indicator of toxicity. The increase is not statistically significant and, when these outliers are omitted, the CRP becomes in-range. In summary, there were no objective signs that the tea was harmful or toxic.

While there has been shown and described the preferred embodiment of the instant invention it is to be appreciated that the invention may be embodied otherwise than is herein specifically shown and described and that within said embodiment, certain variations, modifications, and equivalent arrangements may be made in the form and arrangement of the parts without departing from the underlying ideas or principles of this invention as set forth in the claims appended herewith.

Accordingly, while the present invention has been described herein in detail in relation to one or more preferred embodiments, it is to be understood that this disclosure is only illustrative and exemplary of the present invention and is made merely for the purpose of providing a full and enabling disclosure of the invention. The foregoing is considered illustrative of only the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

The foregoing discussion is illustrative of the invention. However, since many embodiments of the invention can be made without departing from the spirit and scope of the invention, the invention resides wholly in the claims hereinafter appended.

I claim:

1. A beverage composition comprising: 15% tea solids by weight and 85% water by weight, wherein the tea solids comprises about 24-25% carob by weight, about 4-5% anise by weight, about 29-30% *eucalyptus* by weight, and about 40% thyme by weight.

2. The beverage composition as claimed in claim 1, wherein the tea solids comprises about 1-3% honey by weight.

3. The beverage composition as claimed in claim 2, wherein the honey comprises manuka honey.

4. The beverage composition as claimed in claim 1, wherein the tea solids comprise micellized curcumin, wherein the micellized curcumin is in a liquid or a powdered form.

5. The beverage composition as claimed in claim 1, wherein the composition comprises additional ingredients selected from a group consisting of green tea, herb, and manuka honey.

6. A process for preparation of a beverage composition, the process comprising the steps of:

a) adding a composition of tea solids to a prescribed quantity of distilled water;

b) boiling an infusion obtained in step (a) for a first pre-defined time duration;

c) brewing the infusion obtained after step (b) for a second pre-defined time duration;

d) filtering and cooling of the infusion obtained after step (c);

e) decanting the infusion obtained after step (d) into a container to obtain the beverage composition;

f) adding a pre-defined quantity of drops of curcumin to the beverage composition of step (e);

wherein the composition of the tea solids is 15% by weight;

wherein the prescribed quantity of the distilled water is 85% by weight; and wherein the tea solids comprises about 24-25% carob by weight, about 4-5% anise by weight, about 29-30% *eucalyptus* by weight, and about 40% thyme by weight.

7. The process for preparation of the beverage composition as claimed in claim 6, wherein the composition of tea solids comprises leaves, seeds, stems, twigs, vines, pods or other parts of carob, anise, *eucalyptus*, thyme, black tea, and green tea plants.

8. The process for preparation of the beverage composition as claimed in claim 6, wherein the composition of tea solids comprises about 1-3% honey by weight.

9. The process for preparation of the beverage composition as claimed in claim 8, wherein the honey comprises manuka honey.

10. The process for preparation of the beverage composition as claimed in claim 6, wherein the curcumin comprises micellized curcumin.

11. The process for preparation of the beverage composition as claimed in claim 10, wherein the micellized curcumin is in a liquid form.

12. The process for preparation of the beverage composition as claimed in claim 10, wherein the micellized curcumin is in a powdered form.

13. The process for preparation of the beverage composition as claimed in claim 6, wherein the beverage composition comprises additional ingredients selected from a group consisting of green tea, herb, and manuka honey.

14. A beverage composition comprising: 15% tea solids by weight and 85% water by weight, wherein the tea solids comprises about 24-25% carob by weight, about 4-5% anise by weight, about 29-30% *eucalyptus* by weight, about 40% thyme by weight, and about 1-3% honey by weight.

15. The beverage composition as claimed in claim 14, wherein the honey comprises manuka honey.

16. The beverage composition as claimed in claim 14, wherein the tea solids comprise micellized curcumin.

17. The beverage composition as claimed in claim 16, wherein the micellized curcumin is in a liquid form.

18. The beverage composition as claimed in claim 16, wherein the micellized curcumin is in a powdered form.

19. The beverage composition as claimed in claim 14, wherein the composition comprises additional ingredients selected from a group consisting of green tea, herb, and manuka honey.

20. The beverage composition as claimed in claim 14, wherein the tea solids comprises leaves, seeds, stems, twigs, vines, pods or other parts of carob, anise, *eucalyptus*, thyme, black tea, and green tea plants.

* * * * *